(12) United States Patent
Lai et al.

(10) Patent No.: US 8,288,129 B2
(45) Date of Patent: Oct. 16, 2012

(54) METHOD FOR PRODUCING HYALURONIC ACID

(75) Inventors: Horng-Ji Lai, Taipei (TW);
Chien-Cheng Lin, Taipei (TW);
Shang-Ming Lin, Taichung County (TW)

(73) Assignee: Body Organ Biomedical Corp., Taipei City (TW)

( * ) Notice: Subject to any disclaimer, the term of this patent is extended or adjusted under 35 U.S.C. 154(b) by 773 days.

(21) Appl. No.: 12/324,551

(22) Filed: Nov. 26, 2008

(65) Prior Publication Data

US 2009/0137009 A1    May 28, 2009

Related U.S. Application Data

(60) Provisional application No. 60/990,281, filed on Nov. 26, 2007.

(51) Int. Cl.
*C12P 19/04* (2006.01)

(52) U.S. Cl. .......... 435/101; 514/54; 536/55.1
(58) Field of Classification Search .......... 435/101; 514/54; 536/55.1
See application file for complete search history.

(56) References Cited

FOREIGN PATENT DOCUMENTS

JP          05111367    *  5/1993
WO    WO 2007/129828 A1 * 11/2007

OTHER PUBLICATIONS

Gilbert et al., Biomaterials 27, 3675-3683 (2006).*
Hayashi, Electronic translation of JP 05111367 (1993).*

* cited by examiner

*Primary Examiner* — Chih-Min Kam
(74) *Attorney, Agent, or Firm* — Birch, Stewart, Kolasch & Birch, LLP

(57) ABSTRACT

The method for manufacturing hyaluronic acid rich matrix comprises the steps of providing a crest; and decellularizing a tissue of crest to form a decellularized hyaluronic acid rich matrix.

7 Claims, 4 Drawing Sheets

METHOD FOR PRODUCING HYALURONIC ACID

This Nonprovisional application claims priority under 35 U.S.C. §119(e) on Patent Application No(s). 60/990,281 filed on 11/26/2007, the entire contents of which are hereby incorporated by reference.

BACKGROUND OF THE INVENTION (1) Field of the Invention

The present invention relates to a process for producing hyaluronic acid matrix, more particularly, to produce hyaluronic acid matrix by decellularizing the tissue to provide a hyaluronic acid rich acellularization matrix.

(2) Description of the Prior Art

Hyaluronic acid (HA) is a glycosaminoglycan consisting of repeating disaccharides of alternating D-glucuronic acid and N-acetylglucosamine molecules. It is a straight-chained polymer with a molecular weight that varies between 50,000 and 13,000,000 Da.

Hyaluronic acid is naturally present in the pericellular gels, in the fundamental substance of connective tissue and in vertebrate organisms, of which it is one of the chief components, in the synovial fluid of joints, in the vitreous humor, in the human umbilical cord tissues and in rooster combs.

Hyaluronic acid plays a vital role in many biological processes. For example, hyaluronic acid is applied in the tissue repair process, especially in the early stages of granulation, stabilizing the coagulation matrix and controlling its degradation, favoring the recruitment of inflammatory cells such as polymorphonucleate leukocytes, and orientating the successful migration of epithelial cells.

Besides, the application of hyaluronic acid solutions could accelerate healing in patients suffering from sores, wounds and burns. It is also known that hyaluronic acid fractions can be used to facilitate tissue repair, as substitutes for the intraocular fluid, or they can be administered by the intra-articular route to treat joint pathologies.

Because of different producing processes, there are two kinds of hyaluronic acid, one is the isolation-origin HA and the other is the fermentation-origin HA.

The process to produce the isolation-origin HA includes removal of epithelium from the rooster comb, grinding of rooster comb, treatments in acetone and multiple treatments with ethanol and sodium chloride solutions. The process to produce the fermentation-origin HA is by continuous fermentation of *Streptococcus* in a chemostat culture.

The fermentation-origin HA typically includes significant levels of endotoxins and higher levels of bacteria that must be removed. Therefore, it needs to be more purified in order to eliminate as many bacterial proteins as possible. It is to say that the problem of traditional batch culture in which degradation enzymes can begin to break down the cell walls of *Streptococcus* is releasing cell contents into the fermenter broth, leading to purification difficulties.

The isolation-origin HA as produced in biological systems, is associated with proteins and other glycosaminoglycans, so it has to be extensively purified. The complex purification procedures are required in order to obtain a pure product from the sources mentioned above, especially rooster combs, without too much degradation of the molecular chains. Even if very sophisticaed methods for purification and sterilization, have been developed it is inevitable that the molecular weight decreases during these steps and the final product in most cases has much lower molecular weight.

In other words, one important issue of producing isolation-origin HA with this material is the likelihood of it being contaminated by viruses. Complex purification procedures are therefore needed. However, the complex procedures will cost a lot.

SUMMARY OF THE INVENTION

In general, it is an object of the present invention to for manufacturing hyaluronic acid rich matrix.

In one embodiment, the process for manufacturing hyaluronic acid rich matrix comprises the steps of providing a crest of fowls; and decellularizing the tissue of crest to form a decellularized hyaluronic acid rich matrix, wherein the matrix is characterized by reduced immunlogenicity upon placement inside the crest.

It is a further object of the present invention to provide a method for cross-linking the decellularizated hyaluronic acid rich matrix with chemical, physical or other cross-linked methods to modify the properties.

In some aspects, there is provided a hyaluronic acid rich matrix for tissue of the crest comprising steps of removing cellular material from the tissue of the crest, and increasing porosity of the decellularized hyaluronic acid rich matrix, the tissue of the crest being characterized by reduced immunogenicity upon placement inside.

In a preferred embodiment, the tissue of the crest material could be combs, etc. of fowls, such as chicken, turkey, and the like.

It is another object of the present invention to provide a hyaluronic acid rich matrix with mechanical strength to, and it is increased by at least several times more than the matrix derived from crosslinked of hyaluronic acid solution.

BRIEF DESCRIPTION OF THE DRAWINGS

The present invention will now be specified with reference to its preferred embodiment illustrated in the drawings, in which.

DESCRIPTION OF THE PREFERRED EMBODIMENT

Figure 1:
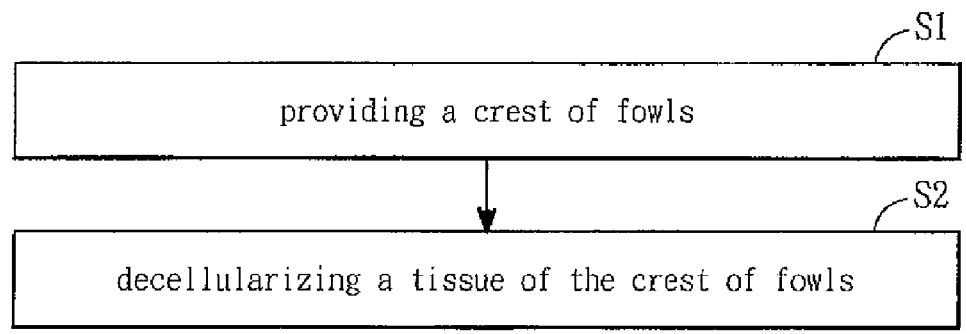
FIG. 1 is a process diagram showing the method for manufacturing hyaluronic acid rich matrix of the present invention.

FIG. 1 shows the method for manufacturing hyaluronic acid rich matrix comprises the step of S1 to provide a crest, and the step of S2 to decellularize the tissue of the crest to form the decellularized hyaluronic acid rich matrix. The decellularized hyaluronic acid rich matrix is characterized by removed all the cells upon placement inside the crest which is the most immunogenic part of animal tissue.

Figure 2:
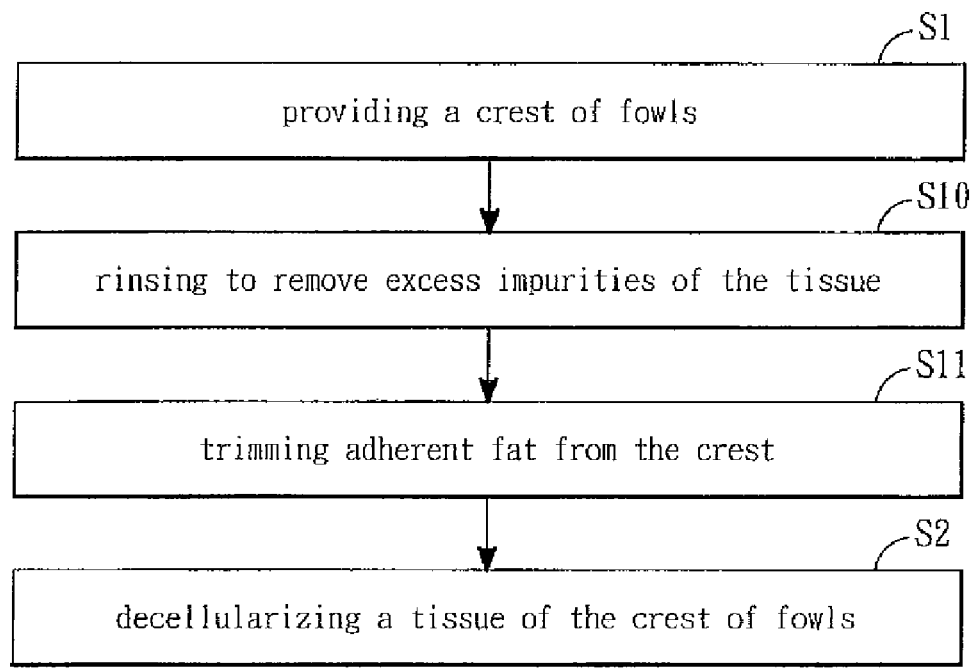
FIG. 2 is a process diagram showing the detail process of the method of FIG. 1 of the present invention.

As shown in FIG. 2, before the step S2 being performed, the step S10 is further included to gently rinse the crest with solution, such as fresh saline, DI water, detergent solution or less than 50% ETOH, to remove excess impurities of tissue, and also the step S11 could be performed to trim adherent fat carefully from the crest.

Figure 3:
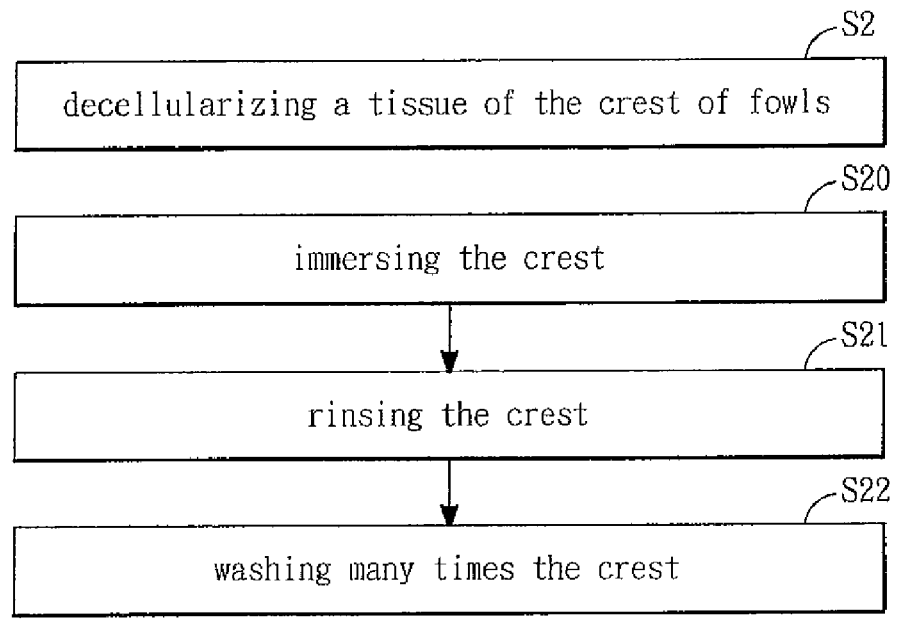
FIG. 3 is a process diagram showing the method for decellularizing the crest of the present invention.
Figure 4:
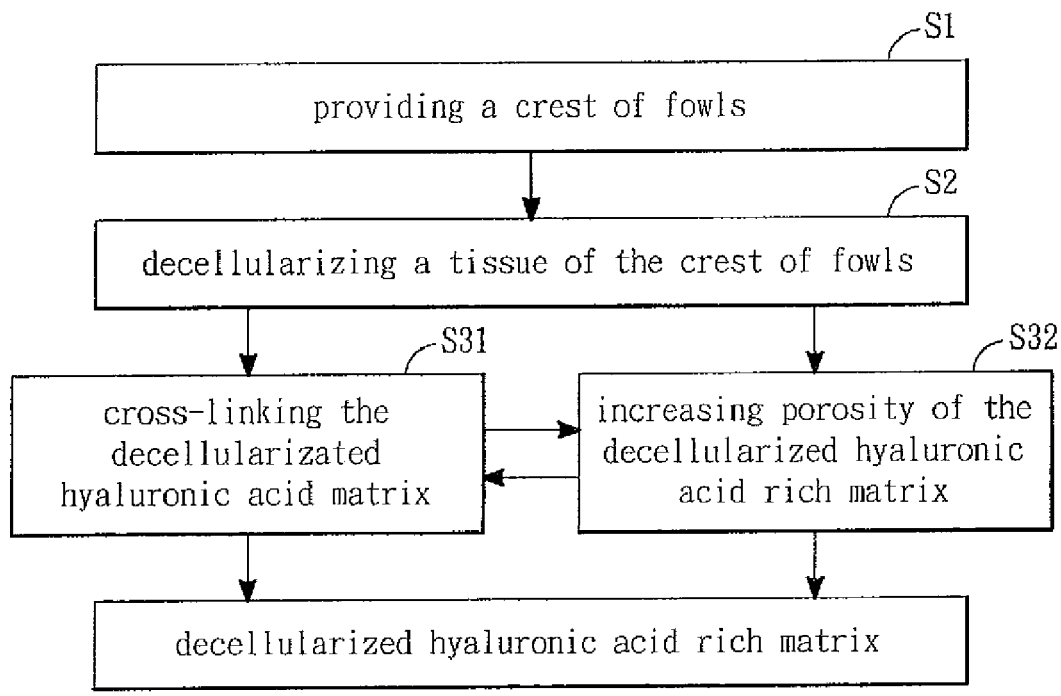
FIG. 4 is a process diagram showing the method after decellularizing the crest of the present invention.

In a preferred embodiment, as shown in FIG. 3, the step S2 to decellularize the tissue of the crest further includes the step S20 to immerse the crest. It is noted that during the step S20 of immersing the crest, it further includes the steps to immerse the crest in a hypotonic tris buffer (pH 7.5-8.5; preferred as pH 8.0) containing a protease inhibitor (phenyl-methyl-sulfonyl fluoride, 0.30-0.40 mg/L; preferred as 0.35 mg/L) for 12-36(24) hours under constant stirring and then to immerse the crest in solution, such as a 0.8-1.2% solution of Triton X-100 (octylphenoxypolyethoxyethanol) or SDS, in tris-buffered salt solution with protease inhibition for 12-36 (24) hours under constant stirring.

After the step S20 being performed, the crest thoroughly is next rinsed and digested in physiological solution (step S21). In one embodiment, the physiological solution can be PBS or Hank's solution. Finally, washing many times the crest for 6 to 48 hours by DI water or PBS as the step 822. It is noted that before the step S22 being done a further 12 to 36 hours (preferred about 24 hours) extraction with Triton X-100 in tris buffer could be performed.

After the step S2 of decellularizing the crest, a step S31 of cross-linking the decellularizing tissue of the crest could be performed to modify the properties.

The step S31 of cross-linking the tissue of the crest is performed by a chemical crosslink method or a physical crosslink method. Each crosslinked methods can increase the mechanical strength and degradation time when applicated inside the physiological enviroment.

For chemical crosslink method, this kind of crosslink method will not only prolong the degradation time in vivo but also increase the mechanical strength. However, the disadvantage of this method is to increase the possibility of immune response. In a embodiment, the chemical crosslink methods are performed by applying a crosslinking agent such as glutaaldehyde, EDC/carbodiimide, genipin or other chemical crosslink agent.

The physical crosslink method could select the group of thermo method, UV method, γ-radiation method or other radiation methods, or combining some or all the above methods. The advantage of the physical crosslink method is lower possibility of immune response compared to chemical crosslink method.

Figure 5:
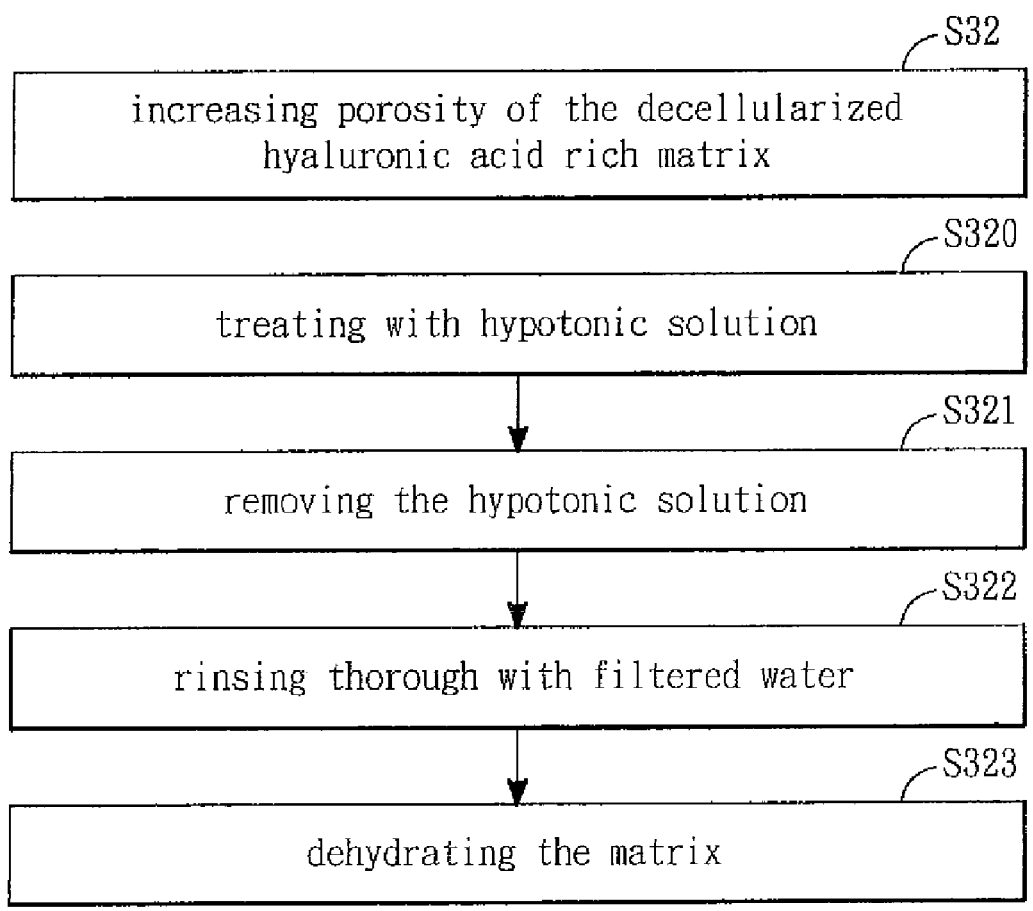
FIG. 5 is a process diagram showing the method for increasing porosity of the decellularized hyaluronic acid rich matrix of the present invention.

FIG. 5 shows that after the step S2 being done, a step S32 could be included to increase porosity of the decellularized hyaluronic acid rich matrix.

The step S32 to increase porosity of decellularized hyaluronic acid rich matrix comprise the further steps of treating with hypotonic solution at room temperature for several hours (S320). After the step S320, a step S321 of removing the hypotonic solution by DI water or physiological solution, such as PBS or Hank's solution. Then a step of S322 is introduced to rinse the tissue of the crest thorough with filtered water. In the end, a step S323 is done to store the matrix of the crest after performing a dehydrating process by lyophilization, however, it is noted that the lyophilization process is optional.

It is noted that the above steps S31 and S32 could be applied interchangeably according to what is need. That means in some circumstance only one of the steps S31 and S32 is selected and performed, and in other circumstance both the steps S31 and S32 are performed. Besides, if it is needed, the step S32 would be performed before the step S31, and vice versa.

Figure 6:
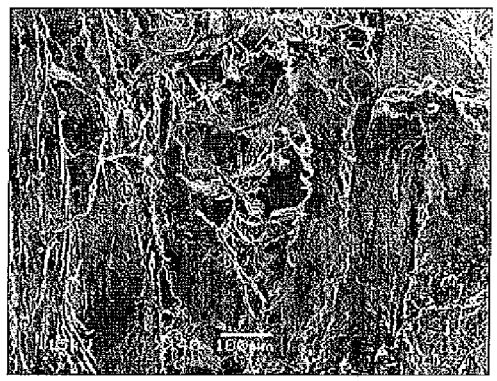
FIG. 6 is the SEM of the decellularized hyaluronic acid rich matrix of the present invention.
Figure 6:
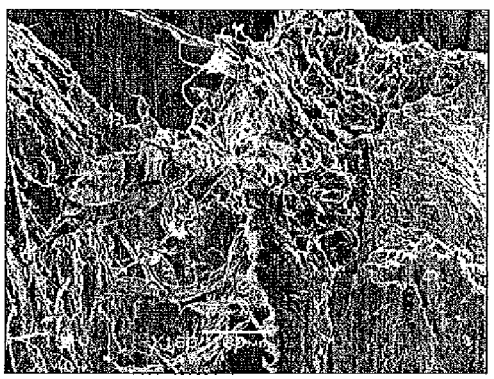
Figure 6:
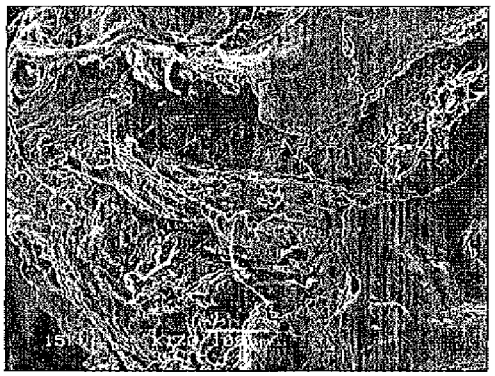
Figure 6:
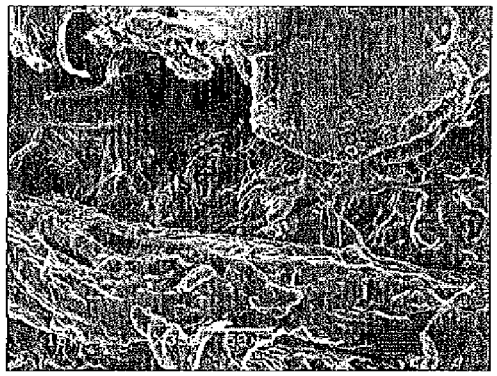

FIG. 6 shows the SEM of the tissue of the crest. It shows the decellularized hyaluronic acid rich matrix after decellulariz-ing, and the tissue of the crest remains well construction, not be damaged by decellularizing.

In one embodiment, the crest is namely comb, etc., and the fowls could be chicken, turkey, or the like.

It is noted that by performing the decellularizing method proposed in the present invention the hyaluronic acid rich matrix would have the mechanical strength up to over 20 kgf, which is about several times than that of the isolation-origin HA or the fermentation-origin HA produced by the conventional method.

Besides, in comparison with the prior art, the isolation-origin HA and the fermentation-origin HA, the present invention has advantages of fewer process and less cost. Because the isolation-origin HA and the fermentation-origin HA both need complex purification procedures therefore the complex procedures will cost a lot. Moreover, it needs more time to complete.

While the preferred embodiments of the present invention have been set forth for the purpose of disclosure, modifications of the disclosed embodiments of the present invention as well as other embodiments thereof may occur to those skilled in the art. Accordingly, the appended claims are intended to cover all embodiments which do not depart from the spirit and scope of the present invention.

What is claimed is:

1. A method for manufacturing hyaluronic acid rich matrix comprises the steps of:
   providing a crest of fowls;
   decellularizing a tissue of said crest to form a decellularized hyaluronic acid rich matrix with tissue of the crest remaining well construction by immersing said crest in a hypotonic solution for 12 hours to 36 hours and immersing said crest in an non-ionic surfactant solution for 12 hours to 36 hours; and
   cross-linking said decellularizated hyaluronic acid rich matrix.

2. The method for manufacturing hyaluronic acid rich matrix of claim 1, wherein said step of cross-linking said decellularizated hyaluronic acid rich matrix is performed by a crosslinking agent which is selected from the group consisting of glutaraldehyde, 1-Ethyl-3-(3-dimethylaminopropyl) carbodiimide/carbodiimide, and genipin.

3. The method for manufacturing hyaluronic acid rich matrix of claim 1, wherein said step of cross-linking said decellularizated hyaluronic acid rich matrix is performed by physical crosslinking methods which is selected from the group consisting of thermo method, uv irradiating method, γ-radiation method.

4. The method for manufacturing hyaluronic acid rich matrix of claim 1, wherein said fowl is a chicken or a turkey.

5. The method for manufacturing hyaluronic acid rich matrix of claim 1, after said step of decellularizing said crest further comprising the step of:
   rinsing said crest in a phosphate buffered saline (PBS) or Hank's solution;
   washing said crest by deionized water to removing any possibly residual PBS or Hank's solution.

6. The method for manufacturing hyaluronic acid rich matrix of claim 1, wherein before said step of decellularizing said crest, further includes the steps of:
   rinsing said crest to remove excess impurities of said tissue; and
   trimming adherent fat from the surface of said crest.

7. The method for manufacturing hyaluronic acid rich matrix of claim 6, wherein said crest is rinsed by a solution selected from the group consisting of a solution of fresh saline, deionized water, detergent solution and less than 50 vol % ETOH.

* * * * *